(12) United States Patent
Lerche et al.

(10) Patent No.: US 8,980,224 B2
(45) Date of Patent: Mar. 17, 2015

(54) METHOD OF CARDIAC IMAGING

(75) Inventors: Mathilde Lerche, Frb. C (DK); Rene Zandt, Sodra Sandby (SE); Klaes Golman, Horsholm (DK); Mikkel Thaning, Oslo (NO); Jan-Henrik Ardenkjaer-Larsen, Buckinghamshire (GB); Stefan Petersson, Helsingborg (SE)

(73) Assignee: GE Healthcare AS, Oslo (NO)

( * ) Notice: Subject to any disclaimer, the term of this patent is extended or adjusted under 35 U.S.C. 154(b) by 2249 days.

(21) Appl. No.: 11/719,585

(22) PCT Filed: Nov. 18, 2005

(86) PCT No.: PCT/NO2005/000434
§ 371 (c)(1),
(2), (4) Date: Jan. 29, 2009

(87) PCT Pub. No.: WO2006/054903
PCT Pub. Date: May 26, 2006

(65) Prior Publication Data
US 2009/0162287 A1   Jun. 25, 2009

(30) Foreign Application Priority Data
Nov. 19, 2004  (NO) .................................. 20045058

(51) Int. Cl.
*A61K 49/06* (2006.01)
*G01R 33/56* (2006.01)
*A61B 5/055* (2006.01)

(52) U.S. Cl.
CPC ............ *G01R 33/5601* (2013.01); *A61K 49/06* (2013.01); *A61B 5/055* (2013.01)
USPC .......................................................... 424/9.3

(58) Field of Classification Search
None
See application file for complete search history.

(56) References Cited

U.S. PATENT DOCUMENTS

| | | | | |
|---|---|---|---|---|
| 5,597,548 A * | 1/1997 | Sherry et al. | ............ | 424/9.3 |
| 6,278,893 B1 * | 8/2001 | Ardenkjæ-Larson et al. | ............ | 600/420 |
| 2003/0194810 A1 * | 10/2003 | Dotsch et al. | ............ | 436/18 |

FOREIGN PATENT DOCUMENTS

WO        99/35508        7/1999

OTHER PUBLICATIONS

K Golman, LE Olsson, O Axelsson, S Mansson, M Karlsson, JS Petersson. "Molecular Imaging Using Hyperpolarized 13C." The British Journal of Radiology, vol. 76, 2003, pp. S118-S127.*

P Gould. "C-13 MR Tracers Show Potential for Functional Diagnostics." Molecular Imaging Outlook, Jun. 2004, 2 pages.*
B Saam, DY Yablonskiy, DS Gierada, MS Conradi. "Rapid Imaging of Hyperpolarized Gas Using EPI." Magnetic Resonance in Medicine, vol. 42, 1999, pp. 507-514.*
DA Herzka, P Kellman, AH Aletras, MA Guttman, ER McVeigh. "Multishot EPI-SSFP in the Heart." Magnetic Resonance in Medicine, vol. 47, 2002, pp. 655-664.*
NM Wilke, MJ Herold, A Zenovich, AE Stillman. "Magnetic Resonance First-Pass Myocardial Perfusion Imaging: Clinical Validation and Future Applications." Journal of Magnetic Resonance Imaging, vol. 10, 1999, pp. 676-685.*
AD Sherry, RL Nunnally, RM Peshock. "Metabolic Studies of Pyruvate- and Lactate-Perfused Guinea Pig Hearts by 13C NMR." The Journal of Biological Chemistry, vol. 260, No. 16, 1985, pp. 9272-9279.*
CB Higgins. "Prediction of Myocardial Viability by MRI." Circulation, vol. 99, 1999, pp. 727-729 and a cover page.*
AS Turner, CW McIllwaith, BL Hull. "Techniques in Large Animal Surgery." Wiley-Blackwell, 1989, 381 pages, The title page, a summary, and p. 40 are included for a total of 3 pages.*
JA Romijn, DL Chinkes, JM Schwarz, RR Wolfe. "Lactate-Pyruvate Inverconversion in Blood: Implications for In Vivo Tracer Studies." American Journal of Physiology, vol. 266(3 Pt 1), Mar. 1994, pp. E334-E340.*
Golman, K., et al., Proceedings of the National Academy of Sciences, (2003), 100(18):10435-10439.
Gould, P., "C-13 MR tracers show potential for functional diagnostics", [online], Jun. 14, 2004, [searched on May 12, 2011], <http://www.diagnosticimaging.com/mri/content/article/113619/1186272>.
PCT/NO2005/000434 Int'l Search Report & Written Opinion dated Jan. 8, 2007.
Golman, Klaes, et.al. "Molecular imaging with endogenous substances" Proceedings of the National Academy of Sciences of the USA, vol. 100, No. 18, Sep. 2, 2003, pp. 10435-10439.
Gould, P. "C-13 MR tracers show potential for functional diagnostics" [Online] Jun. 2004, www.giagnosticimaging.com/molecularimagaingoutlook/2004/jun/04.jhtm.
Golman, K, et.al. "Moleculare imaging using hyperpolarized 13C" British Journal of Radiology, British Institute of Radiology, London, GB. vol. 76, no. spec No. 2 2003, pp. S118-S127.
Khairallah, Maya, et.al. "Profiling substrate fluxes in the isolated working mouse heart using 13C-labeled substrates: focusing on the origin and fate of pyruvate and citrate carbons" American Journal of Physiology. Heart and Circulatory Physiology. Apr. 2004, vol. 286 No. 4, pp. H1461-H1470.
Golman, et.al., "Metabolic imaging and other applications of hyperpolarized 13C" Academic Radiology, Reston, VA, US, vol. 13, No. 8, Aug. 2006 pp. 932-942.

* cited by examiner

*Primary Examiner* — Frederick Krass
*Assistant Examiner* — Isaac Shomer

(57) ABSTRACT

The invention relates to a method of cardiac imaging using hyperpolarised $^{13}$C-pyruvate as MR imaging agent, which allows determination of the viability of cells in the myocardium.

8 Claims, 2 Drawing Sheets

METHOD OF CARDIAC IMAGING

Figure 1:
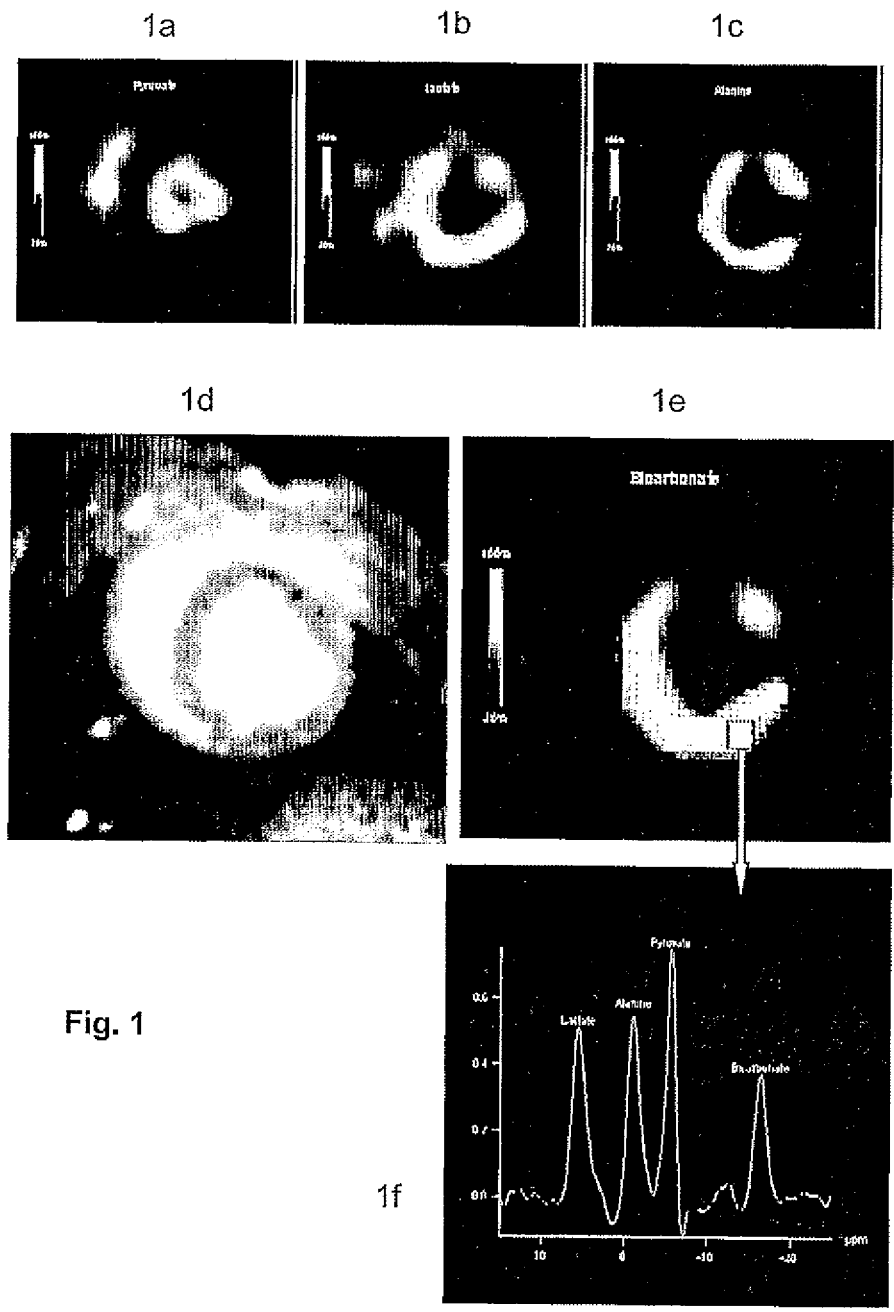

This application is a filing under 35 U.S.C. 371 of international application number PCT/NO2005/000434, filed Nov. 18, 2005, which claims priority to application number 20045058 filed Nov. 19, 2004, in Norway the entire disclosure of which is hereby incorporated by reference.

The invention relates to a method of cardiac imaging using hyperpolarised $^{13}$C-pyruvate as MR imaging agent, which allows determination of the viability of cells in the myocardium.

Magnetic resonance (MR) imaging (MRI) is a imaging technique that has become particularly attractive to physicians as it allows for obtaining images of a patients body or parts thereof in a non-invasive way and without exposing the patient and the medical personnel to potentially harmful radiation such as X-ray. Because of its high quality images, MRI is the favourable imaging technique of soft tissue and organs, as for instance the heart.

Ischemia related injuries and diseases in the heart account for the majority of deaths in the Western countries. Myocardial ischemia is a serious condition and only early rapid identification and location of myocardial ischemia can prevent the patient suffering from irreversible myocardial damages.

Cardiac tissue, like other metabolically active tissue, is particularly vulnerable to ischemic injuries. The initial phase of acute myocardial infarction is in general associated with a loss of normal contractile function, which manifests itself as regional dyskinesia. This may be due to an abrupt fall in coronary perfusion pressure, which induces an acute hibernating state, and to the rapid cessation of normal transmembrane ion transport. Reperfusion of the ischemic myocardium prior to the onset of irreversible injury may lead to a rapid or delayed return (stunning) to normal cardiac metabolism and function.

Magnetic resonance imaging has been established as a useful cardiac imaging technique. Although MR techniques using spin-echo imaging are capable of showing the anatomy of the heart, the use of contrast agents is necessary for the detection of myocardial ischemia and infarction. One class of MR contrast agent are paramagnetic contrast agents, which comprise a paramagnetic metal ion, in the form of a salt or in a complex with a chelating/complexing moiety.

The paramagnetic contrast agent GdDTPA (Magnevist™) has been subject of clinical testing for use in myocardial imaging. Although this metal complex has been shown to improve identification of acute myocardial infarcts on MR images in animals and humans, its clinical use in imaging of the myocardium is limited due to its rapid excretion and distribution within the extracellular fluid space.

$Mn^{2+}$, a paramagnetic metal ion has been used as a contrast agent for use in myocardial MR imaging. It competes with $Ca^{2+}$ for entry in the contracting myocardium through slow $Ca^{2+}$ channels, resulting in a significant shortening of relaxation time $T_1$ and thus increased signal intensity in normal myocardial tissue. The total influx of $Mn^{2+}$ per time unit is raised during increased heart rate and force of contraction. However, in ischemic myocardium, much less $Mn^{2+}$ is taken up because of reduction in blood flow and decrease in contractility. Hence ischemic myocardium can be detected and distinguished form normal myocardial tissue by MR imaging using paramagnetic $Mn^{2+}$ as a contrast agent.

However, the use of $Mn^{2+}$ has certain drawbacks. The use of manganese salts, for instance $MnCl_2$ is associated with a safety risk due to cardiac toxicity of these salts (see for instance Hu et al. Magn. Res. in Medicine 46, (2001), 884-890). Attempts have been made to compensate the toxic effects of manganese salts by either adding calcium salts or by administering the salts in form of a slow infusion. The disadvantage of using calcium in the contrast agent formulation is that it competes with manganese for the calcium channels in entering into the myocytes. This may lead to reduction of efficacy and a subsequent need to inject higher doses of the contrast agent to compensate this effect.

WO-A-99/01162 describes a method of detecting myocardial ischemia using manganese complexes in combination with fast image generation. The imaging procedure is said to be conveniently carried out within a period from 3 to 6 hours post injection. Although this method seems not to be associated with toxicity problems, obtaining results from the imaging procedure is delayed by the relatively long time period between the administration of the contrast agent and the commencement of the imaging procedure. This results in delaying of possibly necessary treatment.

WO 2004/054623 describes a method to identify areas suffering from myocardial ischemia using certain manganese complexes. A physical and/or pharmaceutical stress regime is part of this method as it increases contrast difference between normal and ischemic myocardium and allows thus for the use of lower contrast agent doses. A stress regime however generates additional psychological strain in the patient.

It is therefore a need for an agent to be used in a MR imaging method that allows for the discrimination between ischemic myocardial tissue and normal myocardial tissue thus allowing for an assessment of viability of said tissue on a cellular level. The agent should further have a favourable safety profile, i.e. do not show any toxic side effects at clinical doses. Further, there is a need for a MR imaging method allowing for the rapid and easy assessment of viability of the myocardial tissue without generating additional stress for the patient and without delaying commencement of treatment measures.

WO-A-99/35508 discloses a method of MR investigation of a patient using a hyperpolarised solution of a high $T_1$ agent as MR imaging agent. The term "hyperpolarisation" means enhancing the nuclear polarisation of NMR active nuclei present in the high $T_1$ agent, i.e. nuclei with non-zero nuclear spin, preferably $^{13}$C- or $^{15}$N-nuclei. Upon enhancing the nuclear polarisation of NMR active nuclei, the population difference between excited and ground nuclear spin states of these nuclei are significantly increased and thereby the MR signal intensity is amplified by a factor of hundred and more. When using a hyperpolarised $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. A variety of possible high $T_1$ agents suitable for hyperpolarisation and subsequent use as MR imaging agents are disclosed including but not limited to non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulfonamides. It is further stated that intermediates in normal metabolic cycles such as the citric acid cycle like fumaric acid and pyruvic acid are preferred imaging agents for the imaging of metabolic activity.

It has to be stressed that the signal of a hyperpolarised imaging agent decays due to relaxation and—upon administration to the patient's body—dilution. Hence the $T_1$ value of the imaging agents in biological fluids (e.g. blood) must be sufficiently high to enable the agent to be distributed to the target site in the patient's body in a highly hyperpolarised state.

We have now surprisingly found that hyperpolarised $^{13}$C-pyruvate can be used as a imaging agent for assessing viability of myocardial tissue. The MR signal amplitudes arising from the different pyruvate metabolites vary depending on metabolic state of the myocardial tissue. Hence the unique metabolic peak pattern formed by these metabolites can be used as fingerprint for the metabolic state of the cardiac tissue under examination and thus allows for the discrimination between viable and non-viable myocardial tissue. This makes hyperpolarised $^{13}$C-pyruvate an excellent agent for in vivo MR imaging for assessing the viability of myocardial tissue, e.g. identifying "tissue at risk" after myocardial ischemia or heart attacks. This information which goes beyond perfusion assessment or identification of dead myocardial tissue is important for a physician to commence adequate treatment of a patient to prevent further damage of the myocardium.

Thus, in a first aspect the present invention provides an MR imaging method for assessing the viability of myocardial tissue using hyperpolarised $^{13}$C-pyruvate as a imaging agent $^{13}$C-pyruvate has an excellent safety profile and—as an endogenous compound—well tolerated by the human body. The use of hyperpolarised $^{13}$C-pyruvate in the method of the invention allows for obtaining immediate results as no delay between administration and MR imaging procedure is required. This means that the patient can undergo treatment as soon as possible, thus increasing the chances of survival and recovery. A stress regime is not needed in the method of the invention which is a further benefit for the patients.

Hyperpolarisation of NMR active $^{13}$C-nuclei may be achieved by different methods (e.g. described in WO-A-99/35508), preferred methods are polarisation transfer from a noble gas, "brute force", spin refrigeration, the parahydrogen method and DNP. To obtain hyperpolarised $^{13}$C-pyurvate, it is preferred to either polarise $^{13}$C-pyruvate directly or to polarise $^{13}$C-pyruvic acid and convert the polarised $^{13}$C-pyruvic acid to polarised $^{13}$C-pyruvate, e.g. by neutralisation with a base A preferred way for obtaining hyperpolarised $^{13}$C-pyruvate is the polarisation transfer from a hyperpolarised noble gas. Noble gases having non-zero nuclear spin can be hyperpolarised, i.e. have their polarisation enhanced over the equilibrium polarisation, e.g. by the use of circularly polarised light. A hyperpolarised noble gas, preferably $^3$He or $^{129}$Xe, or a mixture of such gases, may be used to effect hyperpolarisation of $^{13}$C-nuclei. The hyperpolarisation may also be achieved by using an isotopically enriched hyperpolarised noble gas, preferably $^3$He or $^{129}$Xe. The hyperpolarised gas may be in the gas phase, it may be dissolved in a liquid/solvent, or the hyperpolarised gas itself may serve as a solvent. Alternatively, the gas may be condensed onto a cooled solid surface and used in this form, or allowed to sublime. Intimate mixing of the hyperpolarised gas with the compound to be polarised is preferred. Hence, if $^{13}$C-pyruvic acid is polarised, which is a liquid at room temperature, the hyperpolarised gas is preferably dissolved in a liquid/solvent or selves as a solvent. If $^{13}$C pyruvate is polarised, the hyperpolarised gas is preferably dissolved in a liquid/solvent, which also dissolves pyruvate.

Another preferred way for obtaining hyperpolarised $^{13}$C-pyruvate is that polarisation is imparted to NMR active nuclei by thermodynamic equilibration at a very low temperature and high field. Hyperpolarisation compared to the operating field and temperature of the NMR spectrometer is effected by use of a very high field and very low temperature (brute force). The magnetic field strength used should be as high as possible, suitably higher than 1 T, preferably higher than 5 T, more preferably 15 T or more and especially preferably 20 T or more. The temperature should be very low, e.g. 4.2 K or less, preferably 1.5 K or less, more preferably 1.0 K or less, especially preferably 100 mK or less.

Another preferred way for obtaining hyperpolarised $^{13}$C-pyruvate is the spin refrigeration method. This method covers spin polarisation of a solid compound or system by spin refrigeration polarisation. The system is doped with or intimately mixed with suitable paramagnetic materials such as $Ni^{2+}$, lanthanide or actinide ions in crystal form with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The pre-requisite for this method is that the paramagnetic species has a highly anisotropic g-factor. As a result of the sample rotation, the electron paramagnetic resonance will be brought in contact with the nuclear spins, leading to a decrease in the nuclear spin temperature. Sample rotation is carried out until the nuclear spin polarisation has reached a new equilibrium.

In a more preferred embodiment, DNP (dynamic nuclear polarisation) method is used to obtain hyperpolarised $^{13}$C-pyruvate. Polarisation is effected by a paramagnetic compound, the so-called paramagnetic agent or DNP agent. During the DNP process, energy, normally in the form of microwave radiation, is provided, which will initially excite the paramagnetic agent. Upon decay to the ground state, there is a transfer of polarisation from the unpaired electron of paramagnetic agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01/96895, both of which are included by reference herein. To obtain hyperpolarised $^{13}$C-pyruvate by the DNP method, either $^{13}$C-pyruvate and/or $^{13}$C-pyruvic acid can be used as the compound to be polarised.

If $^{13}$C-pyruvic acid and/or $^{13}$C-pyruvate is used depends mainly on the paramagnetic agent employed in the DNP process. If the paramagnetic agent is soluble in $^{13}$C-pyruvic acid, then $^{13}$C-pyruvic acid is preferably used and a liquid mixture, preferably a liquid solution is formed by the paramagnetic agent and $^{13}$C-pyruvic acid. If the paramagnetic agent is not soluble in $^{13}$C-pyruvic acid, then $^{13}$C-pyruvate and/or $^{13}$C-pyruvic acid and at least one co-solvent are used to form a liquid mixture, preferably a liquid solution. It has been found that the success of the DNP and thus the level of polarisation is dependent on the compound to be polarised and the paramagnetic agent being in intimate contact with each other. Hence the co-solvent is preferably a co-solvent or co-solvent mixture that dissolves both, the paramagnetic agent and $^{13}$C-pyruvic acid and/or $^{13}$C-pyruvate. For $^{13}$C-pyruvate water is preferably used as a co-solvent.

Further, it has been found that higher polarisation levels are achieved by the DNP method when the sample mixture upon cooling/freezing forms a glass rather than a crystallized sample. Again, the formation of a glass allows a more intimate contact of the paramagnetic agent and the compound to be polarised. $^{13}$C-pyruvic acid is a good glass former and is therefore preferably used in the DNP process, whenever the paramagnetic agent is soluble in $^{13}$C-pyruvic acid. $^{13}$C-pyruvate is a salt and a liquid mixture of an aqueous solution of $^{13}$C-pyruvate and a paramagnetic agent will result in a crystallized sample upon freezing. To prevent this, it is preferred to add further co-solvents which are good glass formers like glycerol, propanediol or glycol.

Hence in one embodiment, $^{13}$C-pyruvate is dissolved in water to obtain an aqueous solution and a paramagnetic agent, glycerol and optionally a further co-solvent are added to form a liquid mixture. In a preferred embodiment, $^{13}$C-pyruvic acid, a paramagnetic agent and a co-solvent are combined to form a liquid mixture. In a most preferred embodiment, $^{13}$C-pyruvic acid and a paramagnetic agent are combined to form a liquid mixture. Intimate mixing of the compounds can be achieved by several means known in the art, such as stirring, vortexing or sonification.

The liquid mixture is then frozen before the DNP process is carried out. Cooling/freezing of the liquid mixture may be achieved by methods known in the art, e.g. by freezing the liquid mixture in liquid nitrogen or by simply placing it in the polarizer, where liquid helium will freeze the sample.

As described previously, dynamic nuclear polarisation (DNP) is a polarisation method where polarisation of the compound to be polarised is effected by a DNP agent, i.e. a paramagnetic agent/compound.

Many known paramagnetic compounds may be used as DNP agents, e.g. transition metals such as chromium (V) ions, organic free radicals such as nitroxide radicals, trityl radicals or magnetic particles. Such DNP agents are for instance described in WO-A-99/35508, WO-A-88/10419, WO-A-90/00904, WO-A-91/12024, WO-A-93/02711 or WO-A-96/39367.

In a preferred embodiment, a trityl radical of formula (I)

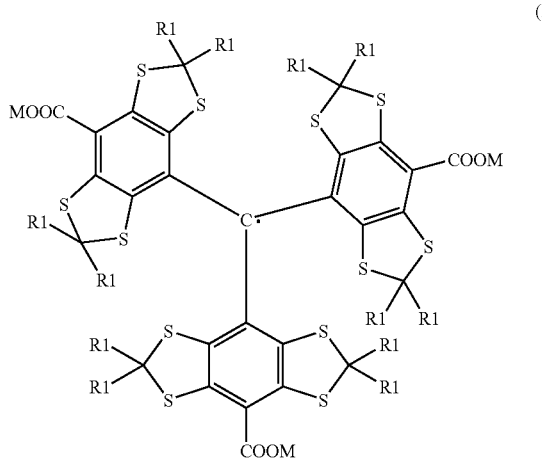

(I)

where
M represents hydrogen or one equivalent of a cation; and
R1 which is the same or different represents a straight chain or branched optionally hydroxylated $C_1$-$C_6$-alkyl group or a group —$(CH_2)_n$—X—R2, wherein n is 1, 2 or 3; X is O or S and R2 is a straight chain or branched, optionally hydroxylated $C_1$-$C_4$-alkyl group.

is used as the paramagnetic agent to obtain $^{13}$C-pyruvate by the DNP method.

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, R1 is the same or different, preferably the same and represents a straight chain or branched optionally hydroxylated $C_1$-$C_4$-alkyl group, most preferably methyl, ethyl, isopropyl, hydroxymethyl or hydroxyethyl.

In a further preferred embodiment, R1 is the same or different, preferably the same and represents —$CH_2$—O—($C_1$-$C_3$-alkyl), —$(CH_2)_2$—O—$CH_3$, —($C_1$-$C_3$-alkyl)-O—$CH_3$, —$CH_2$—S—($C_1$-$C_3$-alkyl), —$(CH_2)_2$—S—$CH_3$, —($C_1$-$C_3$-alkyl)-S—$CH_3$, —$CH_2$—O—$CH_3$, —$CH_2$—O—$C_2H_5$, —$CH_2$—O—$C_2H_4OH$, —$CH_2$—$CH_2$—O—$CH_3$, —$CH_2$—S—$CH_3$, —$CH_2$—S—$C_2H_5$, —$CH_2$—S—$C_2H_4OH$ or —$CH_2$—$CH_2$—S—$CH_3$, most preferably —$CH_2$—$CH_2$—O—$CH_3$.

In a more preferred embodiment, M represents hydrogen or sodium and R1 is the same and represents —$CH_2$—$CH_2$—O—$CH_3$.

The trityl radicals of formula (I) may be synthesized as described in detail in WO-A-91/12024, WO-A-96/39367, WO 97/09633 and WO-A-98/39277. Briefly, the radicals may be synthesized by reacting three molar equivalents of a metallated monomeric aryl compound with one molar equivalent of a suitably protected carboxylic acid derivative to form a trimeric intermediate. This intermediate is metallated and subsequently reacted with e.g. carbon dioxide to result in a tri-carboxylic trityl carbinol which, in a further step, is heated with a strong acid to generate a triarylmethyl cation. This cation is then reduced to form the stable trityl radical.

A liquid mixture comprising $^{13}$C-pyruvate and/or $^{13}$C-pyruvic acid and optionally a solvent preferably contains 5 to 100 mM trityl radicals of formula (I), more preferably 10 to 20 mM, especially preferably 12 to 18 mM and most preferably 13 to 17 mM. It has been found that the build-up time for polarisation in the DNP process is shorter using higher amounts of radical, however, the achievable polarisation level is lower. Hence these two effects have to be balanced against each other.

The DNP technique is for example described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment of the method of the invention, the DNP process is carried out in liquid helium and a magnetic field of about 1 T or above. Suitable polarisation units are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region P near the superconducting magnet where the magnetic field strength is sufficiently high, e.g. between 1 and 25 T, for polarisation of the $^{13}$C nuclei to take place. The sample bore is preferably sealable and can be evacuated to low pressures, e.g. pressures in the order of 1 mbar or less. A sample (i.e. the mixture comprising the paramagnetic agent and $^{13}$C-pyruvate and/or $^{13}$C-pyruvic acid) introducing means such as a removable sample-transporting tube can be contained inside the bore and this tube can be inserted from the top of the bore down to a position inside the microwave chamber in region P. Region P is cooled by liquid helium to a temperature low enough for polarisation to take place, preferably temperatures of the order of 0.1 to 100 K, more preferably 0.5 to 10 K, most preferably 1 to 5 K. The sample introducing means is preferably sealable at its upper end in any suitable way to retain the partial vacuum in the bore. A sample-retaining container, such as a sample-retaining cup, can be removably fitted inside the lower end of the sample introducing means. The sample-retaining container is preferably made of a light-weight material with a low specific heat capacity and good cryogenic properties such, e.g. KelF (polychlorotrifluoroethylene) or PEEK (polyetheretherketone). The sample container may hold one or more samples to be polarised.

The sample is inserted into the sample-retaining container, submerged in the liquid helium and irradiated with microwaves, preferably at a frequency about 94 GHz at 200 mW. The level of polarisation may be monitored by acquiring solid state $^{13}C$-NMR signals of the sample during microwave irradiation, thus the use of a polarising unit containing means to acquire solid state $^{13}C$-NMR spectra in step b) is preferred. Generally, a saturation curve is obtained in a graph showing $^{13}C$-NMR signal vs. time. Hence it is possible to determine when the optimal polarisation level is reached.

If hyperpolarisation is carried out by a method that requires the sample to be in the solid state, e.g. by the DNP method, the solid sample must be transferred into the liquid state to employ it in the method of the invention. The solid polarised mixture is either dissolved, like for instance described in WO-A-02/37132 or melted, as for instance described in WO-A-02/36005. Dissolution of the solid hyperpolarised sample is preferred, more preferred the dissolution in a buffer, preferably a physiologically tolerable buffer, to obtain a liquid composition. The term "buffer" in the context of this application denotes one or more buffers, i.e. also mixtures of buffers.

Preferred buffers are physiologically tolerable buffers, more preferably buffers which buffer in the range of about pH 7 to 8 like for instance phosphate buffer ($KH_2PO_4$/$Na_2HPO4$), N-(2-acetamido)-2-aminoethanesulfonic acid (ACES), piperazine-1,4-bis(2-ethanesulfonic acid) (PIPES), imidazole/HCI, N N-bis 2-hydroxyethyl)-2-aminoethanesulfonic acid (BES), 3-(N-morpholine) propane sulfonic acid monohydrate (MOPS), 4-(2-hydroxyethyl) 1-piperazineethanesulfonic acid (HEPES), 2[(2-hydroxyethyl-1-bis(hydroxymethyl)ethvl)amino]ethanesulfonic acid (TES), tris (hydroxymethyl)aminomethane (TRIS), 4-(2-hydroxyethyl) -piperazineethanesulfonic acid (HEPPS) or piperazine-N,N'-bis(2-hydroxypropanesulfonic acid) dihydrate (TRICINE). More preferred buffers are phosphate buffer and TRIS, most preferred is TRIS. In another embodiment, more than one of the aforementioned preferred buffers, i.e. a mixture of buffers, is used.

When $^{13}C$-pyruvic acid was used as the compound to be polarised, the dissolution also encompasses the conversion of $^{13}C$-pyruvic acid to $^{13}C$-pyruvate. To achieve this, $^{13}C$-pyruvic acid is reacted with a base. In one embodiment, $^{13}C$-pyruvic acid is reacted with a base to convert it to $^{13}C$-pyruvate and subsequently a buffer is added. In another preferred embodiment the buffer and the base are combined in one solution and this solution is added to $^{13}C$-pyruvic acid, dissolving it and converting it into $^{13}C$-pyruvate at the same time. In a preferred embodiment, the base is an aqueous solution of NaOH, $Na_2CO_3$ or $NaHCO_3$, most preferred the base is NaOH In a particularly preferred embodiment, a solution of TRIS buffer containing NaOH is used to dissolve $^{13}C$-pyruvic acid and convert it into the sodium salt of $^{13}C$-pyruvate.

In another preferred embodiment, the buffer or—where applicable—the combined buffer/base solution further comprises one or more compounds which are able to bind or complex free paramagnetic ions, e.g. chelating agents like DTPA or EDTA. It has been found that free paramagnetic ions may cause shortening of the $T_1$ of the hyperpolarised compound, which is preferably avoided.

The dissolution may be carried out by preferably using the methods and/or devices disclosed in WO-A-02/37132. If hyperpolarisation was carried out by the DNP method, a dissolution unit may be used which is either physically separated from the polariser or is a part of an apparatus that contain the polariser and the dissolution unit. In a preferred embodiment dissolution is carried out at an elevated magnetic field to improve the relaxation and retain a maximum of the hyperpolarisation. Field nodes should be avoided and low field may lead to enhanced relaxation despite the above measures.

If hyperpolarisation is earned out by the DNP method, the paramagnetic agent and/or reaction products thereof are preferably removed from the $^{13}C$-pyruvate containing solution. The paramagnetic agent and/or reaction products may be removed partially, substantially or ideally completely, the complete removal is preferred. Reaction products of for instance trityl radicals of the formula (I) might be esters which may be formed upon reaction of pyruvic acid with radicals of formula (I) comprising hydroxy groups. Methods usable to remove the paramagnetic agent and/or reaction products thereof are known in the art. Generally, the methods applicable depend on the nature of the paramagnetic agent and/or its reaction products. Upon dissolution of the solid sample after polarisation, the radical might precipitate and it may easily be separated from the liquid composition by filtration. If magnetic particles are used as paramagnetic agents, these particles are easily removed by filtration as well. If no precipitation occurs, the paramagnetic agent may be removed by chromatographic separation techniques, e.g. liquid phase chromatography like reversed phase or ion exchange chromatography or by extraction.

As trityl radicals of formula (I) have a characteristic UV/visible absorption spectrum, it is possible to use UV/visible absorption measurement as a method to check for its existence in the liquid composition after its removal. In order to obtain quantitative results, i.e. the concentration of the radical present in the dissolved hyperpolarised sample, the optical spectrometer can be calibrated such that absorption at a specific wavelength form a sample yields the corresponding radical concentration in the sample.

The isotopic enrichment of the $^{13}C$-private used in the method of the invention—and/or the $^{13}C$-pyruvic acid which is preferably used to obtain hyperpolarised $^{13}C$-pyruvate by the DNP method, is preferably at least 75%, more preferably at least 80% and especially preferably at least 90%, an isotopic enrichment of over 90% being most preferred. Ideally, the enrichment is 100%. $^{13}C$-pyruvic acid and/or $^{13}C$-pyruvate may be isotopically enriched at the C1-position (in the following denoted $^{13}C_1$-pyruvic acid and $^{13}C_1$-pyruvate), at the C2-position (in the following denoted $^{13}C_2$-pyruvic acid and $^{13}C_2$-pyruvate), at the C3-position (in the following denoted $^{13}C_3$-pyruvic acid and $^{13}C_3$-pyruvate), at the C1- and the C2-position (in the following denoted $^{13}C_{1,2}$-pyruvic acid and $^{13}C_{1,2}$-pyruvate), at the C1- and the C3-position (in the following denoted $^{13}C_{1,3}$-pyruvic acid and $^{13}C_{1,3}$-pyruvate), at the C2- and the C3-position (in the following denoted $^{13}C_{2,3}$-pyruvic acid and $^{13}C_{2,3}$-pyruvate) or at the C1-, C2- and C3-position (in the following denoted $^{13}C_{1,2,3}$-pyruvic acid and $^{13}C_{1,2,3}$-pyruvate); the C1-position being the preferred one.

Several methods for the synthesis of $^{13}C_1$-pyruvic acid and $^{13}C_1$-pyruvate are known in the art. Briefly, Seebach et al., Journal of Organic Chemistry 40(2), 1975, 231-237 describe a synthetic route that relies on the protection and activation of a carbonyl-containing starting material as an S,S-acetal, e.g. 1,3-dithian or 2-methyl-1,3-dithian. The dithian is metallated and reacted with a methyl-containing compound and/or $^{13}CO_2$. By using the appropriate isotopically enriched $^{13}C$-component as outlined in this reference, it is possible to obtain $^{13}C_1$-pyruvate, $^{13}C_2$-pyruvate or $^{13}C_{1,2}$-pyruvate. The carbonyl function is subsequently liberated by use of conventional methods described in the literature. A different synthetic route starts from acetic acid, which is first converted into acetyl bromide and then reacted with $Cu^{13}CN$. The nitril obtained is converted into pyruvic acid via the amide (see for instance S. H. Anker et al, J. Biol. Chem. 176 (1948), 1333 or J. E. Thirkettle, Chem Commun. (1997), 1025). Further, $^{13}C$-pyruvic acid may be obtained by protonating commercially available sodium $^{13}C$-pyruvate, e.g. by the method described in U.S. Pat. No. 6,232,497.

To be used in the method of the invention, the hyperpolarised $^{13}C$-pyruvate is provided as a composition that is suitable for administration to a living human or non-human animal body. The composition preferably comprises a buffer or a mixture of buffers as described above. The composition may further comprise conventional pharmaceutically acceptable carriers, excipients and formulation aids. Thus, the composition may for example include stabilizers, osmolality adjusting agents, solubilizing agents and the like.

Pyruvate is an endogenous compound which is very well tolerated by the human body, even in high concentrations. As a precursor in the citric acid cycle, pyruvate plays an important metabolic role in the human body. Pyruvate is converted into different compounds: its transamination results in alanine, via oxidative decarboxylation, pyruvate is converted into acetyl-CoA and bicarbonate, the reduction of pyruvate results in lactate and its carboxylation in oxaloacetate.

It has now been found that the conversion of hyperpolarised $^{13}C$-pyruvate to hyperpolarised $^{13}C$-lactate, hyperpolarised $^{13}C$-bicarbonate (in the case of $^{13}C_1$-pyruvate, $^{13}C_{1,2}$-pyruvate or $^{13}C_{1,2,3}$-pyruvate only) and hyperpolarised $^{13}C$-alanine can be used for the discrimination between viable and non-viable myocardial tissue using in vivo MR imaging. This is surprising as one has to bear in mind that the $T_1$ of hyperpolarised compounds decays due to relaxation and dilution. $^{13}C$-pyruvate has a $T_1$ relaxation in human full blood at 37° C. of about 42 s, however, the conversion of hyperpolarised $^{13}C$-pyruvate to hyperpolarised $^{13}C$-lactate, hyperpolarised $^{13}C$-bicarbonate and hyperpolarised $^{13}C$-alanine has been found to be fast enough to allow signal detection from the $^{13}C$-pyruvate parent compound and its metabolites. The amount of alanine, bicarbonate and lactate is dependent on the metabolic status of the myocardial tissue under investigation. The MR signal intensity of hyperpolarised $^{13}C$-lactate, hyperpolarised $^{13}C$-bicarbonate and hyperpolarised $^{13}C$-alanine is related to the amount of these compounds and the degree of polarisation left at the time of detection, hence by monitoring the conversion of hyperpolarised $^{13}C$-pyruvate to hyperpolarised $^{13}C$-lactate, hyperpolarised $^{13}C$-bicarbonate and hyperpolarised $^{13}C$-alanine it is possible to study metabolic processes in vivo in the human or non-human animal cardiac tissue by using non-invasive MR imaging.

In the following, the terms "hyperpolarised $^{13}C$-pyruvate", "$^{13}C$-pyruvate" and "pyruvate" are used interchangeably. The same applies to the terms "hyperpolarised $^{13}C$-lactate", "$^{13}C$-lactate" and "lactate"; "hyperpolarised $^{13}C$-alanine", "$^{13}C$-alanine" and "alanine"; "hyperpolarised $^{13}C$-bicarbonate", "$^{13}C$-bicarbonate" and "bicarbonate" and "hyperpolarised $^{13}C$-metabolite(s)", "$^{13}C$-metabolite(s)" and "metabolite(s)".

It has been found that the MR signal amplitudes arising from the different pyruvate metabolites vary depending on metabolic state of the myocardial tissue. Hence the unique metabolic peak pattern formed by alanine, lactate, bicarbonate and pyruvate can be used as fingerprint for the metabolic state of the cardiac tissue under examination and thus allows for the discrimination between viable, non-viable and myocardial tissue at risk. This makes a composition comprising hyperpolarised $^{13}C$-pyruvate an excellent agent for in vivo MR imaging for assessing the viability of myocardial tissue. To determine viability of myocardial tissue is of course important after myocardial ischemia or heart attacks but also in patients with for instance diabetes and metabolic syndrome, both diseases where damages to the myocardial tissue might occur.

As coronary artery disease (CAD) has a variety of clinical presentations, ranging from stable angina to sudden death it is of immediate benefit with a diagnostic method which will report on the viability status of the cells. Between the two most "extreme" conditions—normal viable cells and dead cells, a range of different conditions exists in the ischemic myocardial tissue on cellular level which in turn manifest in said variety of clinical presentations. It is important to identify these different conditions in ischemic myocardial tissue—also called "myocardial tissue at risk", i.e. tissue that if ischemia is prolonged by letting it untreated will become necrotic, to provide the patient with proper treatment to prevent necrosis.

Two different but very severe states of an ischemic heart are hibernation and stunning. Hibernation is a chronic ischemic state in which the myocardial blood flow is reduced and the function of the heart is likewise reduced. The myocardial cells normally oxidize mostly fatty acids. In hibernating cells, there is increased uptake of glucose (known from FDG-PET studies) which suggests that pyruvate will be a preferred substrate for these cells. The stunned myocardium is on the other hand an acute ischemia (e.g. a major coronary occlusion) where the blood flow is normal but the function is decreased. This should result in a low lactate due to relatively low metabolic activity. It has been found that by using the method of the invention myocardial tissue at risk can be identified due to having a low $^{13}C$-bicarbonate and/or a high $^{13}C$-lactate signal.

Ischemia can produce various degrees of myocardial dysfunction, and if severe and prolonged, it will lead to necrosis of the cells. In the latter case the cells are dead and no metabolism is taking place at all, e.g. upon administration of hyperpolarised $^{13}C$-pyruvate, only this signal is expected while no signals from possible metabolites are present in a $^{13}C$-spectrum and/or image.

Generally, the subject under examination, e.g. a patient or an animal, is positioned in the MR magnet. Dedicated $^{13}C$-MR RF-coils are positioned to cover the area of interest.

An imaging medium comprising $^{13}C$-pyruvate and one or more conventional pharmaceutical carriers, excipients and/or additives is administered parenterally, preferably intravenously or intraarterially. Direct administration to the heart is also possible, e.g. by injecting the imaging medium via a catheter placed into the coronary arteries. Dosage and concentration of the imaging medium will depend upon a range of factors such as toxicity and the administration route. Generally, the imaging medium is administered in a concentration of up to 1 mmol pyruvate per kg bodyweight, preferably 0.01 to 0.5 mmol/kg, more preferably 0.1 to 0.3 mmol/kg. The administration rate is preferably less than 10 ml/s, more preferably less than 6 ml/min and most preferable of from 5 ml/s to 0.1 ml/s. At less than 400 s after the administration, preferably less than 120 s, more preferably less than 60 s after the administration, especially preferably 20 to 50 s after the administration and most preferably 30 to 40 s after the administration, an MR imaging sequence is applied that encodes the volume of interest in a combined frequency and spatial selective way. This will result in metabolic images of $^{13}$C-lactate, $^{13}$C-alanine and $^{13}$C-pyruvate and more preferably in metabolic images of $^{13}$C-lactate, $^{13}$C-alanine, $^{13}$C-bicarbonate and $^{13}$C-pyruvate.

The encoding of the volume of interest can be achieved by using so-called spectroscopic imaging sequences as described, in for instance T. R. Brown et al., Proc. Natl. Acad. Sci. USA 79, 3523-3526 (1982); A. A. Maudsley, et al., J. Magn. Res 51, 147-152 (1983). Spectroscopic image data contain a number of volume elements in which each element contains a full $^{13}$C-MR spectrum. $^{13}$C-pyruvate and its $^{13}$C-metabolites all have their unique position in a $^{13}$C-MR spectrum and their resonance frequency can be used to identify them. The integral of the peak at its resonance frequency is directly linked to the amount of $^{13}$C-pyruvate and its $^{13}$C-metabolites, respectively. When the amount of $^{13}$C-pyruvate and each $^{13}$C-metabolite is estimated using time domain fitting routines as described for instance in L. Vanhamme et al., J Magn Reson 129, 35-43 (1997), images can be generated for $^{13}$C-pyruvate and each $^{13}$C-metabolite in which a colour coding or grey coding is representative for the amount of $^{13}$C-pyruvate and each $^{13}$C-metabolite measured.

Although spectroscopic imaging methods have proven their value in producing metabolic images using all kind of MR nuclei e.g. $^1$H, $^{31}$P, $^{23}$Na, the amount of repetitions needed to fully encode the spectroscopic image makes this approach less suitable for hyperpolarised $^{13}$C. Care has to be taken to ensure hyperpolarised $^{13}$C-signal is available during the whole MR data acquisition. At the expense of a reduced signal to noise, this can be achieved by reducing the RF-pulse angle that is applied in every phase encoding step. Higher matrix sizes require more phase encoding steps and longer scan times.

Imaging methods based on the pioneering work by P. C. Lauterbur (Nature, 242, 190-191, (1973) and P. Mansfield (J. Phys. C. 6, L422-L426 (1973)), implying applying a readout gradient during the data acquisition, will allow for higher signal to noise images or the equivalent, higher spatial resolution images. However, these imaging methods in their basic form will not be able to produce separate images for $^{13}$C-pyruvate and its $^{13}$C-metabolites but an image containing the signals of $^{13}$C-pyruvate and all of its $^{13}$C-metabolites, i.e. the identification of specific metabolites is not possible.

In a preferred embodiment, imaging sequences are used that will make use of multi-echoes to code for the frequency information. Sequences that can produce separate water and fat $^1$H-images are for example described in G. Glover, J Magn Reson Imaging 1991; 1:521-530 and S. B. Reeder et al., MRM 51 35-45 (2004). Since the metabolites to be detected and as such their MR frequencies are known, the approach discussed in the references above can be applied to acquire direct images of $^{13}$C-pyruvate, $^{13}$C-alanine and $^{13}$C-lactate and preferably $^{13}$C-pyruvate, $^{13}$C-alanine, $^{13}$C-lactate and $^{13}$C-bicarbonate. This procedure makes more efficient use of the hyperpolarised $^{13}$C-MR signal, giving a better signal quality compared to spectroscopic imaging, a higher spatial resolution and faster acquisition times.

As described earlier, viable cardiac tissue is characterised by a high metabolic activity. Upon ischemia, i.e. decreased blood flow to the tissue, cells are inadequately supplied with oxygen and metabolic processes at cellular level decrease. Surprisingly, it is possible to make this change in metabolism visible within the short MR imaging time window available using hyperpolarised $^{13}$C-pyruvate. Especially significant changes in the $^{13}$C-lactate and $^{13}$C-bicarbonate signal in the myocardial tissue, which depend on the metabolic status of the individual cells, enable evaluation of the viability of the myocardial cells.

Hence in a preferred embodiment, the method according to the invention comprises
(a) acquiring direct $^{13}$C-MR images of $^{13}$C-pyruvate and its $^{13}$C-containing metabolites alanine, lactate and optionally bicarbonate from a subject pre-administered with an imaging medium comprising hyperpolarised $^{13}$C-pyruvate, and
(b) optionally correlating the $^{13}$C signal of a metabolite to the $^{13}$C signal of any other metabolite detected to obtain a contrast based on the difference in signal intensity of two, preferably three, most preferably four $^{13}$C metabolites.
wherein myocardial tissue at risk in said $^{13}$C images is indicated by the lowest $^{13}$C-bicarbonate signal and/or the highest $^{13}$C-lactate signal.

Hence in a further preferred embodiment, the method according to the invention comprises
(a) acquiring direct $^{13}$C-MR images of $^{13}$C-pyruvate and its $^{13}$C-containing metabolites alanine, lactate and optionally bicarbonate from a subject pre-administered with an imaging medium comprising hyperpolarised $^{13}$C-pyruvate, and
(b) optionally correlating the $^{13}$C signal of a metabolite to the $^{13}$C signal of any other metabolite detected to obtain a contrast based on the difference in signal intensity of two, preferably three, most preferably four $^{13}$C metabolites; and
(c) identifying myocardial tissue at risk in said images by identifying the lowest $^{13}$C-bicarbonate signal and/or the highest $^{13}$C-lactate signal.

To correct for the pyruvate signal, both metabolite (lactate, alanine and bicarbonate) and pyruvate images are normalized to the maximum value in each individual image. Second, the normalized lactate image is multiplied by the inverted pyruvate image, e.g. the maximum pyruvate signal in the image minus the pyruvate level for every pixel. As a last step, the intermediate result gained in the operation above is multiplied by the original lactate image.

As an example, to correct for the bicarbonate signal, both lactate and bicarbonate images are normalized to the maximum value in each individual image. Second, the normalized lactate image is multiplied by the inverted bicarbonate image, e.g. the maximum bicarbonate signal in the image minus the bicarbonate level for every pixel. As a last step, the intermediate result gained in the operation above is multiplied by the original lactate image. In a similar manner, the alanine signal may be included in the analysis as well and the finding of a low bicarbonate signal together with an unchanged alanine signal can also be used as an indication for myocardial tissue at risk To emphasise regions with altered metabolism, any combination of increased metabolite signal in connection with a reduced metabolite signal can be used in a similar operation as described in the paragraph above, whereby a weighted metabolite image is obtained. Surprisingly, the assessment of myocardial tissue viability, i.e. the discrimination between viable, damaged and non-viable myocardial tissue is improved by this correction as well.

Anatomical and/or perfusion information may be included in the assessment of myocardial tissue viability according to the method of the invention. Anatomical information may for instance be obtained by acquiring a proton or $^{13}$C-MR image with or without employing a suitable contrast agent. The relative perfusion in the myocardium can be determined by using an MR contrast agent like for instance Omniscan™. Likewise, MR imaging techniques for perfusion measurement without the administration of a contrast agent are known in the art. In a preferred embodiment, a non-metabolised hyperpolarised $^{13}$C-contrast agent is used to determine quantitative perfusion. Suitable techniques and contrast agents are for instance described in WO-A-02/23209. In a more preferred embodiment, hyperpolarised $^{13}$C-pyruvate is used to determine quantitative perfusion.

In another preferred embodiment, the imaging medium comprising hyperpolarised $^{13}$C-pyruvate is administered repeatedly, thus allowing dynamic studies. This is a further advantage of the method according to the invention compared to other MR cardiac imaging methods using manganese based agents which—in higher doses—show cardiotoxic effects. Due to the low toxicity of pyruvate and its favourable safety profile, repeated doses of this compound are well tolerated by the patient.

The results obtained in the method of the invention allow the physician to choose the appropriate treatment for the patient under examination. In a further preferred embodiment, the method of the invention is used to determine whether treatment is successful.

Pyruvate is also reported to have inotropic effects. As such the compound may simultaneously be used as a diagnostic and therapeutic agent in the case of the stunned myocardium where oxygen free radicals are assumed to play a role.

Viewed from a further aspect, the invention provides the use of hyperpolarised $^{13}$C-pyruvate for the manufacture of an imaging medium for use in an MR imaging method for assessing the viability of cells.

The manufacture of an imaging medium containing hyperpolarised $^{13}$C as an imaging agent is described in detail on page 11 to 14.

Viewed from a further aspect the invention provides the use of $^{13C}$-pyruvic acid or $^{13}$C-pyruvate for the manufacture of hyperpolarised $^{13}$C-pyruvate for use as an imaging agent in a MR imaging method for assessing the viability of cells.

The manufacture and preferred embodiments of the manufacture of hyperpolarised 13C-pyruvate from 13C-pyruvic acid or 13C-pyruvate is described in detail on pages 5 to 11.

In a preferred embodiment, the invention provides the use of hyperpolarised $^{13}$C-pyruvate for the manufacture of an imaging medium for use in an MR imaging method for assessing the viability of cells, said method comprising
(a) acquiring direct $^{13}$C-MR images of $^{13}$C-pyruvate and its $^{13}$C-containing metabolites alanine, lactate and optionally bicarbonate from a subject pre-administered with a composition comprising hyperpolarised $^{13}$C-pyruvate,
(b) optionally correlating the $^{13}$C signal of a metabolite to the $^{13}$C signal of any other metabolite detected to obtain a contrast based on the difference in signal intensity of two, preferably three, most preferably four $^{13}$C metabolites.

In a further preferred embodiment, the invention provides the use of $^{13}$C-pyruvic acid or $^{13}$C-pyruvate for the manufacture of hyperpolarised $^{13}$C-pyruvate for use as an imaging agent in a MR imaging method for assessing the viability of cells, said method comprising
(a) acquiring direct $^{13}$C-MR images of $^{13}$C-pyruvate and its $^{13}$C-containing metabolites alanine, lactate and optionally bicarbonate from a subject pre-administered with a composition comprising hyperpolarised $^{13}$C-pyruvate,
(b) optionally correlating the $^{13}$C signal of a metabolite to the $^{13}$C signal of any other metabolite detected to obtain a contrast based on the difference in signal intensity of two, preferably three, most preferably four $^{13}$C metabolites.

The aforementioned method and preferred embodiments of this method are described in detail on page 17 to 20.

EXAMPLES

Example 1

Synthesis of Tris(8-carboxy-2,2,6,6-(tetra(methoxyethyl)benzo-[1,2-4,5']bis-(1,3)dithiole-4-yl)methyl Sodium Salt 10 g (70 mmol) Tris(8-carboxy-2,2,6,6-(tetra(hydroxyethyl)benzo-[1,2-4,5']-bis-(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HQ (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 2

Production of a Composition Comprising Hyperpolarised $^{13}$C-pyruvate by the DNP Method Using $^{13}$C-pyruvic Acid and the Trityl Radical of Example 1

A 20 mM solution was prepared by dissolving 5.0 mg of the radical of Example 1 in $^{13}C_1$-pyruvic acid (164 μl). The sample was mixed to homogeneity and an aliquot of the solution (41 mg) was placed in a sample cup and inserted in the DNP polariser.

The sample was polarised under DNP conditions at 1.2 K in a 3.35 T magnetic field under irradiation with microwave (93.950 GHz). After 2 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarised sodium $^{13}C_1$-pyruvate. The dissolved sample was rapidly analysed with $^{13}$C-NMR to assess the polarisation and a 19.0% $^{13}$C polarisation was obtained.

Example 3

Production of a Composition Comprising Hyperpolarised $^{13}$C-pyruvate by the DNP Method Using $^{13}$C-pyruvic Acid and the Trityl Radical of Example 1

A 15 mM solution was prepared by dissolving the radical of Example 1 (209.1 mg) in a mixture of $^{13}C_1$-pyruvic acid (553 mg) and unlabelled pyruvic acid (10.505 g). The sample was mixed to homogeneity and an aliquot of the solution (2.015 g) was placed in a sample cup and inserted in the DNP polariser.

The sample was polarised under DNP conditions at 1.2 K in a 3.35 T magnetic field under irradiation with microwave (93.950 GHz). After 4 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarised sodium $^{13}C_1$-pyruvate with a total pyruvate concentration of 0.5 M in 100 mM TRIS buffer. In series with the dissolution device a chromatographic column was connected. The column consists of a cartridge (D=38 mm; h=10 mm) containing hydrophobic packing material (Bondesil-C18, 40UM Part #:12213012) supplied by Varian. The dissolved sample was forced through the column which selectively adsorbed the radical. The filtered solution was rapidly analysed with $^{13}$C-NMR to assess the polarisation, 16.5% $^{13}$C polarisation was obtained. The residual radical concentration was subsequently analysed with a UV spectrophotometer meter at 469 nm and was determined to be below the detection limit of 0.1 µM.

Example 4

Production of Hyperpolarised $^{13}$C-pyruvate by the DNP Method Using $^{13}$C-pyruvic Acid and Tris(8-carboxy-2,2,6,6-tetra(hydroxyethoxy)methyl-benzo [1,2-d:4,5-d']bis(1,3)-dithiole-4-yl)methyl Sodium Salt Tris(8-carboxy-2,2,6,6-tetra(hydroxyethoxy)methyl-benzo[1,2-d:4,5-d']-bis-(1,3)-dithiole-4-yl)methyl sodium salt was synthesised as described in Example 29 in WO-A-97/09633.

A 20 mM solution was prepared by dissolving Tris(8-carboxy-2,2,6,6-tetra(hydroxyethoxy)methyl-benzo[1,2-d:4,5-d']-bis-(1,3)-dithiole-4-yl)methyl sodium salt in $^{13}C_1$-pyruvic acid (83.1 mg). The sample was mixed to homogeneity, placed in a sample cup and inserted in the DNP polariser. The sample was polarised under DNP conditions at 1.2 K in a 3.35 T magnetic field under irradiation with microwave (93.950 GHz). The $^{13}$C-NMR signal from the sample was acquired using a Varian Inova-200 NMR spectrometer. The DNP enhancement was calculated from a measurement of the thermal equilibrium $^{13}$C-NMR signal and the enhanced NMR signal. 16% $^{13}$C polarisation was obtained.

Example 5

Cardiac Imaging Procedure According to the Invention 5.1 Pig Preparation

The pig (25 kg) was anaesthetised using a cocktail containing isotonic NaCl (26 vol %), Ketalar (50 mg/ml) (Pfizer AB) (42 vol %), Norcuron (10 mg+5 ml sterile water) (Organon) (21 vol %) and Midazolam (5 mg/ml) (Pharma Hameln) (11% vol) administered using an infusion pump at a rate of 0.6 ml/min.

After the first injection with $^{13}$C-pyruvate the pig was removed from the MR scanner. Under X-ray guidance, a balloon catheter was inserted into the arteria coronaria sinistra and the circumflexa was blocked for a 15 minute period. During the whole operation ECG and blood pressure were measured. 90 Minutes after the end of the ischemic period, the pig was imaged again and $^{13}$C-images were acquired from (about) the same location as were the control measurement was carried out.

5.2 Proton MR Imaging

The pig was positioned in a pig MR coil (Rapid Biomedical, Germany) and imaged using a standard clinical cardiac proton MR imaging sequence library to get anatomical information and to get the short axis view orientation of the myocardium (see proton reference image in the figures to see an example of short axis view).

5.3 $^{13}$C-MR Imaging

Based on the proton frequency found by the MR system the MR frequency for $^{13}C_1$-alanine was calculated according to the following equation:

$$\text{Frequency } ^{13}C_1\text{-alanine} = 0.25144 \times [(\text{system frequency proton} \times 1.00021) - 0.000397708]$$

The frequency calculated positioned the MR signal arising from $^{13}C_1$-alanine on resonance with $^{13}C_1$-lactate on the left and $^{13}C_1$-pyruvate and $^{13}C_1$-bicarbonate resonating on the right of $^{13}C_1$-alanine. An unlocalised MR spectroscopy sequence was run to ensure that the $^{13}$C-MR coil and the system MR frequency had been set up correctly. The $^{13}$C-image location was positioned to cover the myocardium (short axis view) (slice thickness 20 mm, in plane pixel size 7.5×7.5 mm$^2$). In the reconstruction phase, the image data was zero-filled to result in 3.75×3.75×20 mm$^3$ resolution. 16 ml of $^{13}C_1$-pyruvate (327 mM) was injected (0.22 mmol/kg) during a period of 12 s (1.3 ml/s) i.v. into the front leg and 30 s after the start of the injection (i.e. 18 s after finishing the injection), the chemical shift $^{13}$C-MR sequence was started.

5.4 Analysis of the MR Imaging Data

MR imaging resulted in a matrix containing 16×16 elements in which each element or voxel/pixel contains a $^{13}$C-MR spectrum. In the reconstruction phase, the matrix was zero-filled to 32×32, a mathematical operation that helps to improve the spatial resolution. The dataset was analysed on the MRI scanner with software provided by the manufacturer. The results are metabolic images for $^{13}$C-pyruvate, $^{13}$C-alanine, $^{13}$C-lactate and $^{13}$C-bicarbonate.

5.5 Results

The results of the experiment before and after the occlusion of the circumflexa are shown and summarized in attached figures.

FIG. 1 shows images and a spectrum obtained in the pig before the ischemic period with FIG. 1a showing a $^{13}$C-pyruvate image FIG. 1b showing a $^{13}$C-lactate image FIG. 1c showing a $^{13}$C-alanine image FIG. 1d showing a proton reference anatomical image FIG. 1e showing a $^{13}$C-bicarbonate image and FIG. 1f showing a $^{13}$C-NMR spectrum of the pixel selected from the image displayed in FIG. 1e.

Figure 2:
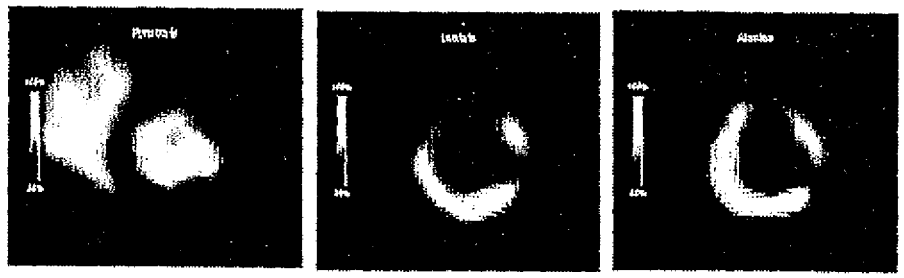
Figure 2:
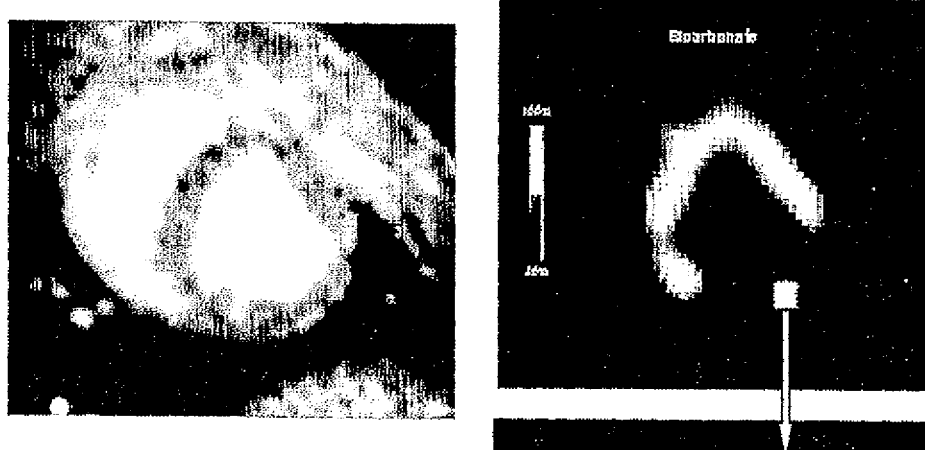
Figure 2:
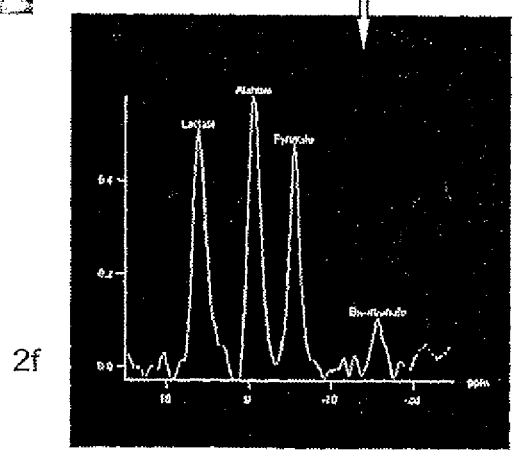

FIG. 2 shows images and a spectrum obtained from the pig after the ischemic period with FIG. 2a showing a $^{13}$C-pyruvate image FIG. 2b showing a $^{13}$C-lactate image FIG. 2c showing a $^{13}$C-alanine image FIG. 2d showing a proton reference anatomical image FIG. 2e showing a $^{13}$C-bicarbonate image and FIG. 2f showing a $^{13}$C-NMR spectrum of the pixel selected from the image displayed in FIG. 2e.

The figures show that there is no difference in the proton reference image before and after the ischemic period. Further a strongly reduced bicarbonate signal (compared to the control) and a positive contrast for the lactate signal indicate the myocardial tissue at risk. No difference is seen in the alanine and pyruvate images before and after the ischemic periods 5.6 Conclusion By use of hyperpolarized $^{13}$C-pyruvate as imaging agent in an MR imaging examination, myocardial tissue at risk can be identified.

What is claimed is:

1. Magnetic Resonance (MR) imaging method for assessing the viability of myocardial tissue, said method comprising
   (a) providing an imaging medium comprising hyperpolarised $^{13}$C-pyruvate,
   (b) administering said imaging medium to a subject,
   (c) acquiring direct $^{13}$C-MR images of $^{13}$C-pyruvate and its $^{13}$C-containing metabolites alanine, lactate and bicarbonate from said subject less than 400 seconds after the administration of the imaging medium comprising $^{13}$C-pyruvate to the subject, wherein each image comprises a matrix containing elements in which each element contains a $^{13}$C -MR spectrum, and wherein each of $^{13}$C-containing pyruvate, alanine, lactate, and bicarbonate are displayed separately
   (d) identifying myocardial tissue at risk in said images by identifying regions in the myocardium with reduced $^{13}$C-bicarbonate signal and/or unchanged $^{13}$C-alanine signal and/or increased $^{13}$C-lactate signal compared to normal myocardial tissue.

2. Method according to claim 1 comprising the step of hyperpolarising $^{13}$C-pyruvic acid and/or $^{13}$C-pyruvate by dynamic nuclear polarization (DNP).

3. Method according to claim 1 wherein the imaging medium comprising $^{13}$C-pyruvate further comprises one or more buffers selected from the group consisting of ($KH_2PO_4$/$Na_2HPO_4$), N-(2-acetamido)-2-aminoethanesulfonic acid (ACES), piperazine-1,4-bis(2-ethanesulfonic acid) (PIPES), imidazole/HCI, N,N-bis(2-hydroxyethyl)-2-aminoethanesulfonic acid (BES), 3-(N-morpholine) propane sulfonic acid monohvdrate (MOPS), 4-(2-hvdroxyethyl) 1-piperazineethanesulfonic acid (HEPES), 2[(2-Hydroxy-1,1-bis(hydroxymethyl)ethyl)amino]ethanesulfonic acid (TES), tris (hydroxymethyl)aminomethane (TRIS), 4-(2-hydroxyethyl)-piperazineethanesulfonic acid (HEPPS) and piperazine-N,N'-bis(2-hydroxypropanesulfonic acid) dihydrate (TRICINE).

4. Method according to claim 1 wherein imaging sequences that make use of multiechoes to code for frequency information are used for acquiring the direct $^{13}$C-images in step c).

5. Method according to claim 1 said method further comprising acquiring proton MRI images with or without a proton MRI contrast agent to determine relative perfusion in the myocardium.

6. Method according to claim 1 said method further comprising acquiring additional $^{13}$C-images with a non-metabolised hyperpolarised $^{13}$C-MR contrast agent to determine quantitative perfusion in the myocardium.

7. Method according to claim 1 said method further comprising acquiring additional $^{13}$C-images with hyperpolarised $^{13}$C-pyruvate to determine quantitative perfusion in the myocardium.

8. Method according to claim 1 wherein the $^{13}$C-pyruvate is a $^{13}$C$_1$-pyruvate.

* * * * *